United States Patent [19]

Edwards

[11] 4,300,240
[45] Nov. 17, 1981

[54] COLD WEATHER FACE MASK

[76] Inventor: Joseph H. Edwards, 7965 Norwood Rd., Salt Lake City, Utah 84121

[21] Appl. No.: 75,265

[22] Filed: Sep. 13, 1979

[51] Int. Cl.³ .......................................... A41D 13/00
[52] U.S. Cl. ..................................................... 2/206
[58] Field of Search .......................... 2/206, 9, 203, 91

[56] References Cited

U.S. PATENT DOCUMENTS

| 766,963 | 8/1904 | Murray | 2/206 X |
| 3,768,100 | 10/1973 | Colman et al. | 2/9 |
| 4,095,290 | 6/1978 | O'Brien | 2/9 |

FOREIGN PATENT DOCUMENTS 366884  8/1906  France ..................................... 2/206

*Primary Examiner*—Peter P. Nerbun
*Attorney, Agent, or Firm*—Trask & Britt

[57] ABSTRACT

A mask member is made from a thin, rubber, cloth-like material. The mask member is sized and shaped to fit about the face to extend rearward from the face to about the left and right ear areas and to extend in length from an upper edge to a lower edge. The upper edge extends along a line between the cheekbone area below the temples, along the lower part of the eye sockets, contouredly over the bridge of the nose. The mask member is unitarily formed with a nose piece contoured to fit over the nose. The nose piece together with the face mask are shaped to form a breathing aperture for the nostrils. A seam extends from below the nose piece downward to act as a front edge. The seam extends convexly from below the nose to the chin area to form a pocket for the lips and air, and arcuately inward under the chin to the lower edge. The seam selectively forms a channel in communication with the pocket. Aperture means are formed in the mask member proximate the mouth for breathing and speech. Securing means are adapted to the mask member to secure the mask in place.

10 Claims, 3 Drawing Figures

COLD WEATHER FACE MASK

BACKGROUND OF THE INVENTION

1. Field

This invention relates to cold weather apparel. In particular, this invention provides for a cold weather face mask particularly suitable for use by skiers.

2. State of the Art

A variety of protective facial masks or cold weather masks are known. For example, U.S. Pat. No. 766,963 (Murray) shows a muffler. U.S. Pat. No. 731,135 (Scott) shows a different type of neck and ear mechanism. U.S. Pat. No. 2,276,612 (Ellis); 2,573,537 (Bouffard) and 3,768,100 (Colman) all show other forms or types of neck and face protective wear.

The facial protective wear heretofore known, such as those disclosed in the above-referenced patents, all seek to provide insulation and protection against cold weather and wind in coordination with other apparel worn by the user. For example the patent to Murray shows straps passing over the top of the head to provide a means of securing and holding the muffler device in place without interfering with the wearing of a hat. The patent to Scott discloses a device which extends down below the chin into the coat to further provide protection against cold weather elements. The devices disclosed in the above-identified patents, as well as other items which are available on the market, do not effectively integrate themselves with present day apparel typically used in the outdoor winter environment. Further, the devices heretofore known do not take into account certain inherent biological considerations, such as water vapor in the breath of the user and a tendency of that water vapor to condense out on the mask in the vicinity of the mouth and freeze. That is, today a knitted cap is readily available on the market which totally surrounds the head. It has apertures for the eyes and for the mouth. In use, the water vapor in the breath tends to condense on the edges of the aperture provided for the mouth and tends to freeze. The condensed water vapor may cause itching and if its freezes extreme discomfort to the user. Frozen water vapor (ice) may touch the skin causing substantial deterioration of the effectiveness of the mask. Further, knitted masks of the type just described, as well as other masks such as those hereinabove disclosed, are fabricated from conventional cloths, materials which do not adequately insulate or protect against wind. Wind can in fact penetrate through knitted materials, as well as other closer woven materials.

SUMMARY OF THE INVENTION

A cold weather face mask has a mask member made of a thin, rubber cloth-type material. The mask member is sized and shaped to fit about the face to extend in width rearward from the face to about the left and right ear areas and to extend in length from an upper edge to a lower edge. The upper edge extends along a line between the cheekbone area below the temples and along the lower part of the eye socket areas contouredly over the bridge of the nose. The mask member is unitarily formed with a nose piece which angulates outwardly and downwardly at an angle to proximate the angulation of the nose. The nose piece is contoured to fit over the nose and is sized to extend from the upper edge to about the tip of the nose. The mask member is formed with a middle edge in the area above the upper lip which extends essentially the width of the nose piece which, together with the nose piece, form a breathing aperture for the nostrils. The mask member has a seam joined by means which acts as a front edge. The front edge extends from the middle edge convexly to a chin area to form a pocket for the lips and air. The front edge continues from the chin area arcuately inward under the chin to the lower edge to selectively form a channel in communication with the pocket. The mask member has aperture means formed therein proximate the mouth for breathing and speaking. The face mask includes securing means adapted to the mask member to secure the mask member to the face of a user.

In one embodiment, the securing means is comprised of a left and right extension member respectively adapted to the mask member and sized to extend rearward from the left and right rear areas to together surround the head passing at the base of the skull. The securing means also has coacting fastening means adapted to the ends of the extension members for fastening the ends thereof together to secure the mask member to the face of the user.

The lower edge of the mask member preferably extends along a line commencing at its midpoint at about the intersection of the neck with the under chin area and extending rearward on both sides of the head to the area below the rear of the jaw substantially parallel to the collar line. The front end extends from the middle edge to the lower edge substantially along the center line of the face. Preferably, the front edge at the lower edge extends arcuately away from the skin of the user.

In a preferred embodiment, the left and right extensions are unitarily formed with the mask member and are substantially the same length. The lower edge preferably slopes upward from the area below the rear of the jaw and the upper edge preferably slopes downward from the area in front of the ears so that the extensions are narrow bands having substantial parallel upper and lower edges at the ends thereof.

In another preferred embodiment, the middle edge extends beyond the width of the nose piece a short preselected distance to form slits at both ends of said middle edge in said mask member. The nose piece is also sized to extend slightly past the tip of the nose.

The aperture means is preferably a plurality of small apertures formed in the mask in a preselected pattern having a width and a height related to the width and the height of a mouth. The fastening means preferably consists of adjustable coacting velcro strips attached proximate the ends of the bands. The cold weather mask is preferably unitarily formed of a thin rubber cloth-like material which is nylon covered close cell sponge neoprene.

BRIEF DESCRIPTION OF THE DRAWINGS

In the drawings, which illustrate the best mode presently contemplated for carrying out the invention.

DESCRIPTION OF THE ILLUSTRATED EMBODIMENT

Figure 1:
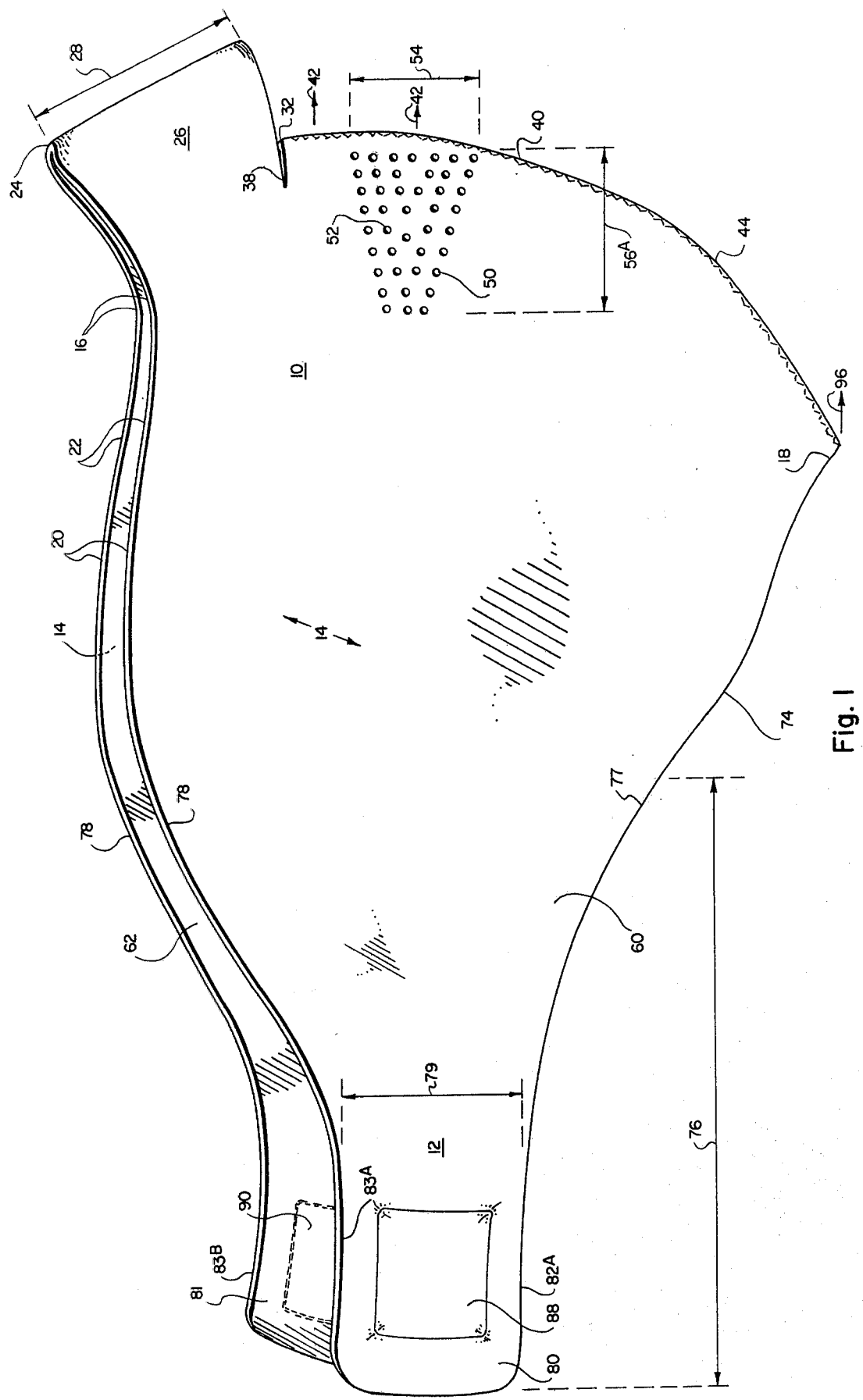
FIG. 1 is a side view of a cold weather face mask of the instant invention.

Referring to the drawings, the cold weather face mask of the instant invention has a mask member 10 and securing means 12. The mask member 10 is sized and shaped to fit about the face to extend in width rearwardly from the face to about the left and right ear areas 14 (FIG. 2) and in length from an upper edge 16 to a lower edge 18. The upper edge 16 extends along a line extending between the cheekbone area below the temples 20 and along the lower part of the eye sockets 22 (FIG. 3) contouredly over the bridge of the nose 24.

Figure 2:
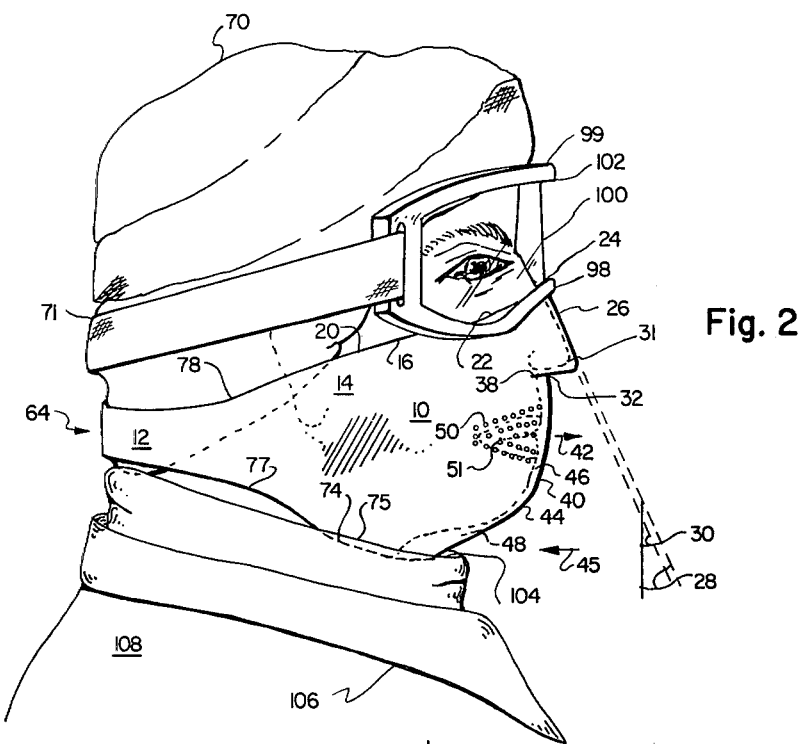
FIG. 2 is a side view of the cold weather face mask of the instant invention positioned about the head and face of a user.

The mask member 10 is unitarily formed with a nose piece 26. The nose piece 26 angulates outwardly and downwardly at an angle 28 which proximates the angle 30 of the nose. The angles 28 and 30 shown in FIG. 2 are shown to be identical. However, the identical nature of the angles is strictly for illustration purposes. It is well known that the angulation of the nose will vary from person to person. The nose piece 26 extends in length 28 from the upper edge 16 to about preferably slightly past or beyond the tip of the nose 31. The amount the piece 26 extends past or beyond the nose tip 31 varies with the user, but should be about one-fourth (¼) inch.

Figure 3:
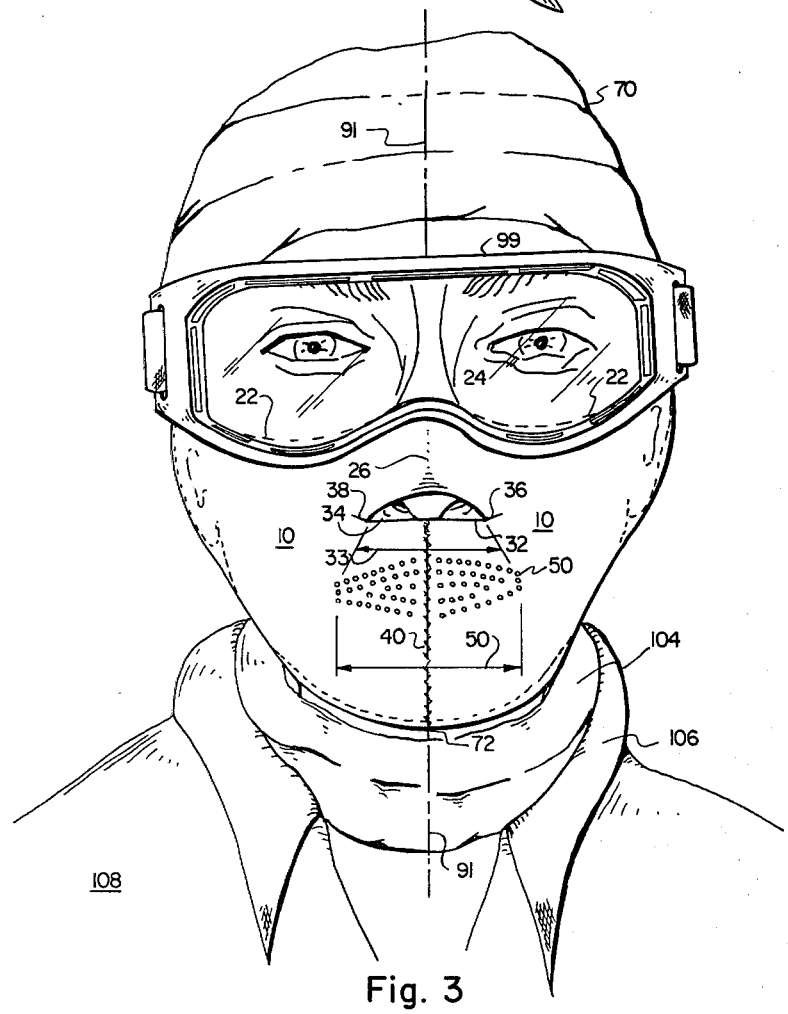
FIG. 3 is a front view of a cold weather face mask of the instant invention positioned about the face and head of a user.

The mask member 10 is formed to have a middle edge 32 in the area above the upper lip. The middle edge 32 extends essentially the width 33 of the nose piece 26, as best seen in FIG. 3. The nose piece 26, together with the middle edge 32, form a breathing aperture 34 for the nostrils. It can be also seen in FIG. 3 that the middle edge 32 is extended beyond the width of the nose piece to form slits 36 and 38. The slits 36 and 38 here formed extend from about ¼ inch to about 1 inch, and preferably about ⅜ inch outward from the width 33 of the nose piece. The slits 36 and 38 allow the nose piece 26 to flex outwardly to accommodate the nose shape of various users. That is, the slits 36 and 38 act so that the angle 28 of the nose piece 26 may readily vary to adapt easily to users. The slits 36 and 38, together with an elastic characteristic of the preferred material of construction, accommodates a wide range of nose shapes without causing discomfort to the user.

The mask member 10 has a seam 40 which acts as a front edge of the mask member 10. The seam or front edge 40 extends from the middle edge 32 convexly or outwardly 42 to a chin area 44 to form a pocket 46 (FIG. 2) for the lips of the user and for air. The seam or front edge 40 extends arcuately from the chin area 44 inward 45 under the chin to the lower edge 18. The seam or front edge 40 selectively forms a channel 48 in communication with the pocket 46. With the mask installed or positioned about the face, the user can manipulate the mask by moving facial muscles, including the jaw, and/or install the mask somewhat loosely so that air can pass up through the channel 48 into the air pocket 46 for use in the process of breathing. A user may so act to preheat the air to be inhaled. The air passing through the channel can obtain heat from the body (skin) without causing discomfort. In severe cold, cold air inhaled directly can cause discomfort and even pain. The preheating capability of the channel provides the user with an option to avoid the pain or discomfort. Similarly, air can be exhausted through the air pocket and channel, which in turn provides heated air for warmth and comfort to the user.

The mask member 10 also has aperture means 50 formed therein proximate the mouth 51 for breathing and speaking. The aperture means 50 is preferably a plurality of small apertures 52 formed in a preselected pattern having a height 54 and a width 56 proximate the size of the mouth 51. The width 56A in FIG. 1 is only ½ the width with the aperture 50 which extends symmetrically on the left side, which is not shown. A plurality of apertures 52 is preferred because it permits breathing and speech to be effected efficiently without providing an edge for the buildup of frozen water vapor. Frozen water vapor ice frequently forms along edges of masks known in the art. The ice touches the skin causing extreme discomfort and in fact defeating the very purpose of the mask.

The securing means 12 is preferably comprised of a left extension member 60 and a right extension member 62. The extension members are respectively adapted to the mask member 10 and sized to extend rearward from the left and right ear areas 14 to together surround the head passing at the base of the skull 64. It is highly preferred that the extension members 60 and 62 pass at the base of the skull 64. In so passing, they avoid interferring with other garments or apparatus, such as goggles. Further, by passing at the base of the skull 64, the extension members or securing means reside or are positioned in the indentation formed between the base of the skull and the commencement of the nape of the neck. Accordingly, a snug, yet not necessarily tight, fit is effected which practically cannot slip. Further, the extension members 60 and 62 simultaneously increase the insulation or protection against the elements and also hold the hat 70 of the user, which typically is positioned to extend into the base of the skull area 64 in place. Also, securing the mask at the base of the skull avoids interference with goggle straps 71.

The lower edge 18 of the mask member 10 preferably extends along a line commencing at its midpoint at about the intersection of the neck with the underchin 72. The line extends rearward on both sides of the head to the area below the rear of the jaw 74 substantially parallel to the collar line 75 (FIG. 2). Most preferably the left and right extensions 60 and 62 are unitarily formed with the mask member 10 and are substantially the same length 76. The lower edge 18 preferably slopes upward 77 from the area below the rear of the jaw 74. The upper edge 16 preferably slopes downward 78 from the area in front of the ears 14 so that the said extensions 60 and 62 are narrow bands having a width 79 at their ends 80 and 81 with upper and lower edges 82A and 83A (82B (not shown) 83B) substantially parallel, as shown. The securing means also includes fastening means which preferably consists of adjustable coacting velcro strips 88 and 90 attached to the ends 80 and 81. The strips 88 and 90 provide for adjustability in length 76 and, in turn, provide flexibility in sizing and loose/tight control means for the user.

It may be noted that the front edge 40 at the lower edge 18 extends arcuately outward 96 away from the skin or neck of the user. The arcuate shape of the front edge 40 at the lower edge 18 prevents chaffing when the mask 10 is in use. The front edge or seam 40 preferably extends approximately along the centerline of the face 91.

It may be particularly noted from FIGS. 2 and 3 that the cold weather mask of the instant invention is particularly adapted for use with apparel presently used today in cold weather environments by skiers, snowshoers, and people similarly attired and similarly involved in outdoor activities. In particular, the upper edge 16 of the mask extends high enough on the face so that conventional goggles, when installed, overlap and hold the upper edge 16 in place. However, the upper edge is not so high on the face to interfere with vision. Further, the mask 10 moves the lower edge or lower rim 98 of the goggles 99 away from the skin of the user which tends to minimize fogging by reducing the amount of body heat transmitted through to the goggle lens 100.

The hat 70 of the user is typically or conventionally a knitted hat which may be known as a ski hat or cap. In cold weather, the hat is typically pulled down low over the forehead and on some occasions tucked under the upper rim 102 of the goggles. The hat 70 is typically positioned to extend downward from the eyebrow area over the ears to the base of the skull 64 to provide maximum protection and to provide warmth to the user. The upper edge 16 of the ski mask extends rearward from the eye socket area 22 to cover the cheekbone so that in coordination with the hat or cap 70, the amount of skin exposed to the elements may be none or nominal depending upon the desires of the user.

It may also be noted that the nose piece 26 extends contouredly up to the bridge of the nose 24. Thus, the lower rim 98 of the goggles 99 will sit on top of the nose piece 26 to hold it in place and provide protection over the entire front of the face.

The lower edge 18 runs along a proximate collar line 75 from the front edge 40 to the area below the rear of the jaw. From that point it extends upward to form the extensions 60 and 62. If the user is wearing a turtleneck sweater, which is a frequently used item of apparel by skiers and other persons outdoors, the turtleneck sweater has a collar line 104 (75) which extends above and provides a sealing along the lower edge 18 from the front edge 40 to the point below the jaw 74. Typically, the user will have a collar 106 of a coat 108 pulled snugly up behind the neck to the base of the skull 64 to provide for sealing along the back of the head to the area below the ears 74. This is not shown in FIG. 2 to provide better illustration of the mask positioned about the head of the user.

The mask is made of a rubber cloth type material. Preferably, it is made of a nylon covered close cell sponge neoprene, which is about one-eighth inch (⅛") thick. The nylon covered close cell sponge neoprene is highly preferred in that it provides excellent insulation and is comfortable to the skin. That is, many users have difficultly wearing wool face masks or similar cloth materials because they become itchy or otherwise find them uncomfortable. For example, wearing a pair of goggles over knitted material can many times create impressions in the skin from the yarn which can become uncomfortable. The close cell sponge neoprene precludes such discomfort. The use of nylon covered close sponge neoprene is also preferred because of the ease of manufacture. That is, the mask can be readily formed without the need to have seams along the upper edge and lower edge. The front edge or seam is preferably joined by stitching after the mask is formed. Using nylon covered close cell neoprene is also highly preferred because it acts as an insulation device, is flexible, or elastic to take into account facial contours of different users and to provide for snug fitting about the head, and because it provides a good aesthetic external appearance.

It is to be understood that the embodiments of the invention herein described are merely illustrative of the application of the principals of the invention. Reference herein to details of the illustrated embodiment is not intended to limit the scope of the claims, which themselves recite those features regarded as essential to the invention.

I claim:

1. A cold weather face mask comprised of:
   a mask member made of a thin rubber cloth type material which is sized and shaped to fit about the face to extend in width rearward from the face to about the left and right ear areas and to extend in length from an upper edge to a lower edge, wherein
   said upper edge extends along a line extending between the cheekbone area below the temples and along the lower part of the eye socket areas contouredly over the bridge of the nose,
   said mask member is unitarily formed with a nose piece which angulates outwardly and downwardly at an angle to proximate the angulation of the nose, said nose piece being contoured to fit over the nose and being sized in length to extend from said upper edge to about the tip of the nose,
   said mask member has a middle edge in the area above the upper lip which extends essentially the width of the nose piece and which together with the nose piece forms a breathing aperture for the nostrils,
   said mask member has a seam joined by means which acts as a front edge to extend convexly from the middle edge to a chin area to form a pocket for the lips and air, and from the chin area arcuately inward under the chin to the lower edge to selectively form a channel in communication with said pocket, and wherein
   said mask member has aperture means formed therein proximate the mouth for breathing and speaking; and
   securing means adapted to the mask member to secure the mask member to the face of a user.

2. The cold weather mask of claim 1 wherein said securing means is comprised of a left and right extension member respectively adapted to the mask member and sized to extend rearward from the left and right ear areas to together surround the head passing at the base of the skull, and coacting fastening means adapted to the ends of the extension members for fastening the ends thereof together and to secure the mask member to the face of a user such that the upper edge forms a seal with the face.

3. The cold weather mask of claim 2 wherein said lower edge extends along a line commencing at its midpoint at about the intersection of the neck with the under chin and extending rearward on both sides of the head to the area below the rear of the jaw substantially parallel to the collar line.

4. The cold weather mask of claim 3 wherein said front edge extends from the middle edge to the lower edge substantially along the center line of the face, and wherein said front edge at said lower edge extends arcuately away from the skin of the user.

5. The cold weather mask of claim 4 wherein left and right extensions are unitarily formed with the mask member and are substantially the same length, and wherein said lower edge slopes upward from the area below the rear of the jaw and the upper edge slopes downward from the area in front of the ears so that the said extensions are narrow bands having substantially parallel upper and lower edges at the ends thereof.

6. The cold weather mask of claim 5 wherein said middle edge extends beyond the width of said nose piece a short preselected distance to form slits at both ends of said middle edge in said mask member, and wherein said nose piece extends slightly past the tip of the nose.

7. The cold weather mask of claim 6 wherein said aperture means is a plurality of small apertures in a preselected pattern having a width and a height aproximately the width and height of the mouth.

8. The cold weather mask of claim 7 wherein said fastening means consists of adjustable coacting velcro strips attached proximate the ends of said extension members.

9. The cold weather mask of claim 7 wherein said bands have a width from about one-half an inch ($\frac{1}{2}''$) to about three inches ($3''$), and wherein said aperture means has a height from about one-half an inch ($\frac{1}{2}''$) to about two and one-half inches ($2\frac{1}{2}''$) and a width from about two inches ($2''$) to about four inches ($4''$).

10. The cold weather mask of claim 7 wherein said thin rubber cloth type material is nylon covered close cell sponge neoprene.

* * * * *